United States Patent
Bhuyan et al.

(10) Patent No.: US 9,622,987 B2
(45) Date of Patent: Apr. 18, 2017

(54) SYNERGISTIC PHARMACEUTICAL COMPOSITION USEFUL FOR THE TREATMENT OF LUNG CANCER

(75) Inventors: Mantu Bhuyan, Jorhat (IN); Pranab Ram Bhattacharyya, Jorhat (IN); Pranab Kumar Baruah, Jorhat (IN); Nabin Chandra Barua, Jorhat (IN); Paruchuri G. Rao, Jorhat (IN); Sushmita Bhattacharya, Santiniketan (IN); Rakesh Kundu, Santiniketan (IN); Priyajit Chatterjee, Santiniketan (IN); Soma Seal, Santiniketan (IN); Sandeep Mukherjee, Santiniketan (IN); Suman Dasgupta, Santiniketan (IN); Sudipta Moitra, Santiniketan (IN); Shelley Bhattacharya, Santiniketan (IN); Samir Bhattacharya, Santiniketan (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/410,844

(22) PCT Filed: Sep. 5, 2012

(86) PCT No.: PCT/IN2012/000581
§ 371 (c)(1),
(2), (4) Date: Jul. 24, 2015

(87) PCT Pub. No.: WO2014/002104
PCT Pub. Date: Jan. 3, 2014

(65) Prior Publication Data
US 2015/0328170 A1 Nov. 19, 2015

(30) Foreign Application Priority Data

Jun. 25, 2012 (IN) .......................... 1949/DEL/2012

(51) Int. Cl.
*A01N 31/00* (2006.01)
*A61K 31/045* (2006.01)
*A61K 36/54* (2006.01)

(52) U.S. Cl.
CPC ............ *A61K 31/045* (2013.01); *A61K 36/54* (2013.01)

(58) Field of Classification Search
CPC ... A61K 31/045; A61K 2300/00; A61K 36/54
See application file for complete search history.

(56) References Cited

PUBLICATIONS

Muchtaridi et al, Majalah Farmasi Indonesia, 16(1), 63-69, 2005.*
OncoLink, Lung Cancer Recurrence, May 8, 2013.*
Freshney (Culture of Animal Cells, A Manual of Basic Technique, Alan R. Liss, Inc., 1983, New York, p. 4).*
Dermer (Bio/Technology, 1994, 12:320).*
Gura (Science, v278, 1997, pp. 1041-1042).*
Muchtaridi et al, Majalah Farmasi Indonesia, 16(1), 63-69, 2005 translated.*

* cited by examiner

*Primary Examiner* — Jean Cornet
(74) *Attorney, Agent, or Firm* — Baker and Hostetler LLP (57) ABSTRACT

The present invention relates to a synergistic pharmaceutical composition comprising Compound C2 (Neo-isopulegol), C3 (Iso-pulegol) and C4 (Citronellol) derived from herbal seed extract of *Litsea cubeba* useful for the treatment of lung cancer. The present invention also relates to the activity of compounds C2 or C3 or C4 either alone or in combination in killing of A549 lung cancer cells.

4 Claims, 6 Drawing Sheets

Fig. 7

SYNERGISTIC PHARMACEUTICAL COMPOSITION USEFUL FOR THE TREATMENT OF LUNG CANCER

RELATED APPLICATIONS

This application is the U.S. national stage of International (PCT) Patent Application PCT/IN2012/000581, filed Sep. 5, 2012, which claims priority to Indian Patent Application No. 1949/DEL/2012, filed Jun. 25, 2012, the entire contents of which are herein incorporated by reference.

FIELD OF THE INVENTION

The present invention relates to a synergistic pharmaceutical composition useful for the treatment of cancer. More particularly, the present invention relates to synergestic pharmaceutical composition comprising compound C2 (Neo-isopulegol), C3 (Iso-pulegol) and C4 (Citronellol) having beneficial destroying activity on non small cell lung carcinoma cell line A-549. The present invention further relates to evaluating the synergistic effect of C2, C3, and C4 combination against lung cancer cell line. Importantly, these compounds had no hazardous effect on normal cells like hepatocytes, adipocytes and skeletal muscle cells and thus are considered to be therapeutically highly relevant.

BACKGROUND OF THE INVENTION

Transformation of a normal cell to malignant derivatives is a multistep process that reflects genetic alterations and defects in normal cell proliferation and homeostasis. A fundamental aspect of cancer is unregulated cell cycle control. Unlike normal cells, which only proliferate in response to developmental or other mitogenic signals which is required for tissue growth, the proliferation of cancer cells proceeds without any regulation. Malignant cells also undergo the same cell cycle stages but the checkpoints of cell cycle remain functionless. Cancer cells proliferate because they are insensitive to growth inhibitory signals arising from the stroma or from gene expression pattern changes consequent to 'terminal' differentiation, nor do they necessarily require extrinsic growth factors to maintain their proliferative state. Cancer is a manifestation of alterations in cell physiology that dictate uncontrolled cell proliferation. Characteristics of cancer cells include unresponsiveness to programmed cell death, insensitivity to antigrowth signals, independent of growth stimulatory signals, uncontrolled replicative potential and persistent angiogenesis.

Cancer cells have defects in regulatory mechanism that govern normal cell proliferation and homeostasis. Mutation in p53 tumor suppressor gene is a common incident in many human cancers. In normal cells, low levels of p53 is maintained by Mdm2. Mdm2 directly suppress p53 by unmasking its nuclear export signal and its subsequent degradation in cytosol. Elevation of p53 level occurs in response to cellular stress such as DNA damage and that leads to cell cycle arrest and apoptosis. Upon sensing DNA damage, p53 phosphorylates and stabilizes, where it acts as a transcription factor for target genes like p21 a cyclin-dependent kinase inhibitor, Bax a proapoptotic member of the Bcl2 family of proteins, DNA repair proteins and also its own regulator Mdm2. p53 also triggers apoptosis by activating Bax and Bak proapoptotic proteins [Yee, 2005].

Normal cells require mitogenic growth signals to enter the proliferative stage whereas cancer cells show uncontrolled proliferation. When quiescent cells enter cell cycle, cyclin D1 is induced in response to mitogenic signals and cyclinD1 assemble with their catalytic partners CDK4 and CDK6 as cell cycle progress through $G_0$ to $G_1$ phase. Constitutive activation of cyclinD1 contributes to the oncogenic transformation of cancer cells. p21 blocks cell cycle progression by inhibiting cyclin-CDK complex and mediates the p53-dependent cell cycle $G_1$ phase arrest [Sherr, 1999].

Since major objective of an anti-cancer drug is to induce apoptosis in cancer cells by triggering caspase activity where a cascade of events ultimately leads to the death of cells, discussed herein below are the prior art on these aspects.

During apoptosis, cells undergo morphological changes: the cell shrinks, shows deformities and looses contact with its neighbouring cells. Chromatin condensation takes place near the nuclear membrane, externalization of phosphatidyl serine occurs in the plasma membrane and finally the cell is fragmented into compact membrane-enclosed structures, called apoptotic bodies. The most important mechanism that occurs during apoptosis is the activation of proteolytic enzymes which eventually leads to DNA fragmentation. Multitude of specific protein substrates responsible for the maintenance of integrity and shape of the cytoplasm or other organelles undergo cleavage [Saraste, 2000].

Caspases play a pivotal role during apoptosis by degenerating the cell structure, eg. by the destruction of nuclear lamina. During apoptosis, nuclear laminae are cleaved at a single site by caspases leading to nuclear membrane breakdown and contributing to chromatin condensation. Caspases also play a significant role in cellular reorganization indirectly by cleaving several proteins involved in cytoskeleton regulation. Caspases ultimately induces cell death and helps in balancing cellular homeostasis.

The present study was undertaken to assess the antiproliferative and apoptotic potentiality of different herbal compounds in lung cancer cells and to determine the underlying molecular mechanism behind apoptotic cell death. Several anti-cancer compounds have the potential to suppress cell proliferation but in the present global scenario where cancer is emerging as the greatest threat to human being, specific active compounds are needed which have precise targets.

The present invention is based on herbal source and is important in the sense that the compounds isolated are volatile and therefore can be inhaled. Further, it is desirable that the ideal molecules would select only malignant cells and would not have any impact on normal cells. It may be noted that there is no report on the synergistic effect of compounds present in the *Litsea cubeba* seed oils and particularly the three compounds used in the present invention in relation to anti-cancer activities. Also, this is for the first time that the vapor of these three compounds isolated from the seed oil of *Litsea cubeba* has been shown to possess strong anti cancer activities against four cancer cell lines.

Thus, keeping in view the hitherto reported prior art, it may be summarized that the most important requirement as of date is to provide herbal pharmaceutical compositions having anticancer activity which do not have detrimental effects on other body cells. Further, till date there is no report on synergism in relation to the said oils towards anticancer activity.

OBJECTIVES OF THE INVENTION

The main object of the present invention is to provide a synergistic pharmaceutical composition comprising compound C2 (Neo-isopulegol), C3 (Iso-pulegol) and C4 (Citronellol) having anti-cancer activity.

Another object of the present invention is to provide pharmaceutical composition comprising compound C2 (Neo-isopulegol), C3 (Iso-pulegol) and C4 (Citronellol) from Litsea cubeba which possess strong anti-cancer activities against cancer cell lines in vapour form.

Still another object of the present invention is to provide three oil compounds C2 (Neo-isopulegol), C3 (Isopulegol) and C4 (Citronellol) which produce a combined vapor that showed maximum anti-cancer activity, therefore demonstrating synergism in killing the cancer cells.

Yet another object of the present invention is to provide therapeutic active compounds having pharmaceutical importance that trigger cell cycle arrest and apoptotic cell death in lung cancer cells without affecting normal cells.

BRIEF DESCRIPTION OF THE DRAWING

FIG. 1 shows-effect of combined vapor (CVp), extracted from Litsea cubeba seeds, on the viability of A549 cells by MTT assay.
(A) A549 lung cancer cells were exposed for 72 h with different dilutions ($10^6$ to $10^2$) of crude oil. Cell viability was measured by using MTT (3-(4,5-Dimethylthiazol-2-yl)-2,5-diphenyltetrazolium bromide) assay and is expressed as % of cell survival relative to control.
(B) Litsea cubeba seed extract was characterized and identified of four major compounds namely Citronellal (C1), Neo-isopulegol (C2), Isopulegol (C3) and Citronellol (C4).
(C) Percentage of cell death was observed when A549 cells were unexposed (control) or exposed with crude extract or with individual compound C1 or C2 or C3 or C4 at $2\times10^2$ dilution.
(D) Effect of CVp (CVp=C2+C3+C4 as 1:1:1) on cell death was observed at 72 h and taking control as without any exposure, visualized by microscopic images.
(E) Cell survivability was measured at different time interval (24, 48, 72 h) with CVp incubations on cells. Values are means±SEM of 3 individual experiments.
*p<0.01; **p<0.01 versus control and #p<0.05 versus C4.

FIG. 2 represents CVp induced apoptosis in A549 lung cancer cells
(A) Apoptotic cell death was examined by Annexin V-Cy3 and CFDA (5(6)-Carboxyfluorescein) double staining method. A549 cells treated with CVp for 36 h showed both green and red stains whereas control (untreated) cells stained green only.
(B) Loss of mitochondrial membrane potential was observed in A549 cells at 36 h exposure of CVp by JC-1 staining assay. Control cells kept in unexposed condition.
(C) Apoptotic DNA fragmentation was observed by CVp treated A-549 cells while control cells (without any exposure) showed no such DNA fragmentation on 1.5% agarose gel electrophoresis. DNA ladder marker was used for the detection of low molecular weight fragments. Figures are representative image of one of the three independent experiments.

FIG. 3 represents CVp induced apoptotic cell death by caspase activation
(A) A549 lung cells were cultured on sterile 22-mm glass cover slips. Mitotracker and FITC (Fluorescein isothiocyanate) conjugated cytochrome C were co-localized in control cells while after 36 h exposure of CVp causes notable release of cytochrome C from the mitochondria.
(B) Immunoblot analysis was done by using anti-cleaved caspase-9 or caspase-3 antibodies in A-549 cells incubated in the presence of CVp at 0 h, 24 h, 36 h time intervals. β-actin used as internal control.
(C) At the same time A549 cell lysates of different incubations were used to observe caspase 3 activity by using proluminescent caspase 3 as the substrate followed by measuring luminescence intensity in a luminometer.
(D) PARP (Poly (ADP-ribose) Polymerase) cleavage was also observed by immunoblot analysis by probing with anti-PARP antibody, β-actin was used as a loading control.

FIG. 4 (A, B) A-549 cells were treated without (control) or with CVp and cells were lysed at different time periods and subjected to immunoblot analysis of Cyclin D1 or pNFkB p65 (Ser-536). (C) Protein levels of pMdm2, p21 and p53 was also analyzed at same period. β-actin used as internal loading control.
(D) Cyclin D1-p21 interaction was increased with time hour due to CVp treatment, which was shown by co-immunoprecipitation study.
(E) Control and CVp treated A-549 cells were analysed for BrdU (5-bromo-2'-deoxyuridine) incorporation and that was observed by florescence microscopic images.
(F) Cell cycle arrest was shown by FACS (Fluorescence-activated cell sorter) analysis of untreated (con) and CVp treated A549 cells.

FIG. 5 represents CVp inhibited Akt phosphorylation
(A,B) Immunoblot analysis of total Akt and phospho-Akt (p-Akt) at $Thr^{308}$ and $Ser^{473}$ in A549 cells treated with CVp for the indicated time period (0 h, 12 h, 24 h and 36 h). Fold change represents the phosphorylation level of the CVp treated cells relative to the control cells. Bands were quantified by densitometric analysis which showed significant increase of phosphorylation of Akt (*p<0.01) and normalized against total Akt level. β-actin served as loading control.

FIG. 6 represents Deactivation of Bad with subdued Bcl-xL level occurred in CVp treated A549 cells
(A) Western blot analysis was performed with control and CVp treated A-549 cells to evaluate the level of p-Bad (ser-136) and Bad protein at different time intervals (12 h, 24 h, 36 h). β-actin served as internal control. Fold change represents the phosphorylation level of Bad the CVp treated cells relative to the control cells. Bands were quantified by densitometric analysis where p-Bad level was compared with Bad level.
(B) Bcl-xL and Bax protein level was also observed in the same manner. Densitometry analysis showed Bcl-xL was negatively correlated with Bax level at 36 h incubation of A549 cells with CVp.

SUMMARY OF THE INVENTION

The plant Litsea cubeba used for the purposes of the present invention was procured from CSIR-NEIST, Jorhat campus. Mature seeds of the plant were considered for the study.

Accordingly, the present invention provides a synergistic pharmaceutical composition useful for the treatment of cancer wherein the said composition comprising compound C2 (Neo-isopulegol), C3 (Isopulegol) and C4 (Citronellol) in a ratio of 1:1:1.

In an embodiment of the present invention, the compounds are derived from ripe seeds of the plant *Litsea cubeba*.

In another embodiment of the present invention, the said compounds are administered individually or in synergistic pharmaceutical composition in the vapor form to induce cell death in the lung cancer cell line by apoptosis.

Yet another embodiment of the present invention, present invention further provides a process for the isolation of anticancer compounds from *Litsea cubeba* wherein the said process comprising the steps of:

[a] dipping ripe seeds of *Litsea cubeba* in distilled water followed by extracting using a Clavenger apparatus for 5 to 7 hours;

[b] separating essential oil deposited above the water layer of step [a];

[c] drying essential oil as obtained in step (b) over anhydrous sodium sulphate (neutral) followed by filtration to give 2 to 3% oil;

[c] subjecting the crude oil as obtained in step [c] to chromatographic purification in a silica gel (20 gm, 100-200 mesh, Rankem) column (1 inch diameter & 50 cm length) packed in hexane to obtain 30 ml fractions which were collected in the following order: fractions 1-10 (hexane), 11-20 (1% Ethyl acetate in hexane), 21-35 (2% Ethyl acetate in hexane), 36-60 (3% Ethyl acetate in hexane), and fraction 61-until completion of the elution of the compounds (4% Ethyl acetate in hexane);

[d] combining fractions 11-20 as obtained in step [c] followed by concentrating in a rotary evaporator to give an oil which was identified as citronellal C1;

[e] combining fractions 23-35 as obtained in step [c] followed by concentrating in a rotary evaporator to give an oily substance which was identified as neo-isopulegol;

[f] combining fractions 40-60 as obtained in step [c] followed by concentrating in a rotary evaporator to give an oily residue which was identified as iso-pulegol;

[g] combining fractions 64-76 as obtained in step [c] followed by concentrating to give a thick oil which was identified as citronellol.

In still another embodiment of the present invention, the said compound C4 (Citronellol) is effective in killing lung cancer cells.

In yet another embodiment of the present invention, the said compounds C2, C3 & C4 in combination (Neo-isopulegol+Isopulegol+Citronellol) are highly effective in killing lung cancer cells, A-549.

In still another embodiment of the present invention, the anti-cancerous activity of the compounds is due to programmed cell death or apoptosis as determined by JC-1 mitochondrial membrane potential assay, DNA fragmentation assay and Annexin V-Cy3/6CFDA dual staining.

In yet another embodiment of the present invention, the compounds having anticancerous activity follow apoptetic pathway as evidenced by caspase 9 and caspase 3 activities measured qualitatively and quantitatively.

In still another embodiment of the present invention, the compounds induce cell cycle arrest by increasing tumor suppressor p53 and its target p21 which abrogates cyclin D1 activity due to enhanced binding with p21 in lung cancer cells.

Yet another embodiment of the present invention, percentage of cell death of the said composition is 90.0±5.6 for lung cancer cell line.

DETAILED DESCRIPTION OF THE INVENTION

Fresh ripe seeds of *Litsea cubeba* wt. 250 gm, collected in the month of August-October 2010 from CSIR-NEIST experimental farm, Jorhat, were dipped in distilled water and extracted using a Clavenger apparatus for 6 hours. The essential oil deposited above the water layer was separated using a separating funnel and dried over anhydrous sodium sulphate (neutral) and filtered to give oil (6.25 gm, 2.5% yield). The thin layer chromatography of the crude oil on silica gel plates indicated the presence of four distinct spots. The crude oil (1 gm) was subjected to chromatographic purification in a silica gel (20 gm, 100-200 mesh, Rankem) column (1 inch diameter & 50 cm length) packed in hexane. 30 mL Fractions were collected in the following order: fractions 1-10 (hexane), 11-20 (1% Ethyl acetate in hexane), 21-35 (2% Ethyl acetate in hexane), 36-60 (3% Ethyl acetate in hexane), and fraction 61-until completion of the elution of the compounds (4% Ethyl acetate in hexane).

Fractions 11-20 containing C1 (TLC) were combined and concentrated in a rotary evaporator to give an oil (100 mg) and this was identified as citronellal from comparison with authentic material (TLC, IR, NMR, MS). Fractions 23-35 containing C2 (TLC) were combined and concentrated in a rotary evaporator to give an oily substance (86 mg) and was identified as neo-isopulegol by comparison of its $^1$H NMR spectrum with that reported in the literature. Fractions 40-60 containing C3 (TLC) were combined and concentrated in a rotary evaporator as explained earlier to give an oily residue (120 mg) and this was identified as isopulegol by direct comparison with $^1$H NMR spectrum with that reported in the literature. Fractions 64-76 containing C4 (TLC) were combined and concentrated to give thick oil (55 mg) which was identified as citronellol from comparison of its $^1$H NMR spectrum with authentic sample.

EXAMPLES

The following examples are given by way of illustration and therefore should not be construed to limit the scope of the present invention.

Example 1

*Litsea* crude seed extract and its fractions comprising compounds C1 (Citronellal), C2 (Neo-isopulegol), C3 (Isopulegol) and C4 (Citronellol) were isolated from the essential oil of the plant that induces cell cycle arrest and apoptosis in lung cancer cell line.

Fresh ripe seeds of *Litsea cubeba* wt. 250 gm, collected in the month of October 2010 from CSIR-NEIST experimental farm, Jorhat, were dipped in distilled water and extracted using a Clavenger apparatus for 6 hours. The essential oil deposited above the water layer was separated using a separating funnel and dried over anhydrous sodium sulphate (neutral) and filtered to give oil (6.25 gm, 2.5% yield). The thin layer chromatography of the crude oil on silica gel plates indicated the presence of four distinct spots. The crude oil (1 gm) was subjected to chromatographic purification in a silica gel (20 gm, 100-200 mesh, Rankem) column (1 inch diameter & 50 cm length) packed in hexane. 30 mL Fractions were collected in the following order: fractions 1-10 (hexane), 11-20 (1% Ethyl acetate in hexane), 21-35 (2% Ethyl acetate in hexane), 36-60 (3% Ethyl acetate in hexane), and fraction 61-until completion of the elution of the compounds (4% Ethyl acetate in hexane). Fractions 11-20 containing C1 (TLC) were combined and concentrated in a rotary evaporator to give an oil (100 mg) and this was identified as citronellal from comparison with authentic material (TLC, IR, NMR, MS). Fractions 23-35 containing C2 (TLC) were combined and concentrated in a rotary evaporator to give an oily substance (86 mg) and was identified as neo-isopulegol by comparison of its $^1$H NMR spectrum with that reported in the literature. Fractions 40-60 containing C3 (TLC) were combined and concentrated in a rotary evaporator as explained earlier to give an oily residue (120 mg) and this was identified as isopulegol by direct comparison with $^1$H NMR spectrum with that reported in the literature. Fractions 64-76 containing C4 (TLC) were combined and concentrated to give thick oil (55 mg) which was identified as citronellol from comparison of its $^1$H NMR spectrum with authentic sample.

Figure 1A:
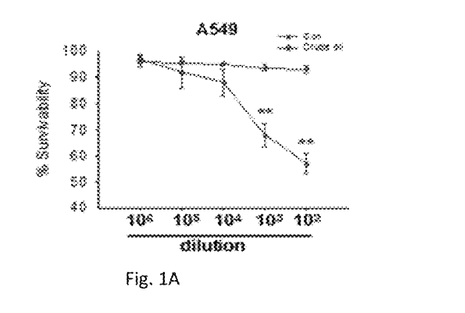
Figure 1B:
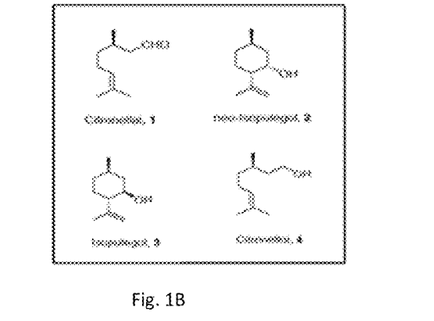

The crude extract thus obtained was characterized and four major compounds were isolated. The chemical compounds were further characterized and identified as Citronellal (C1) (henceforth referred as compound 1), Neo-isopulegol (C2) (henceforth referred as compound 2), Isopulegol (C3) (henceforth referred as compound 3), and Citronellol (C4) (henceforth referred as compound 4), (FIG. 1B).

Compound 1: (Citronellal)

IR (CHCl$_3$): u 2925, 1724, 1457, 1437, 1219, 1040, 772 cm$^{-1}$; $^1$H NMR (CDCl$_3$, 300 MHz): δ 0.96 (d, J=6.6 Hz, 3H, —CHMe), 1.30-138 (m, 2H, —CHMeCH$_2$CH$_2$—), 1.68 (s, 3H, =CMe), 1.98 (s, 3H, =CMe), 1.98-2.06 9 m, 3H, =CCH$_2$— & —CHMe-), 2.24 (dd, J=7.9, 2.6 Hz, 1H, —CHHCHO), 2.37 (dd, J=5.4, 1.6 Hz, 1H, —CHHCHO), 5.06 (t, J=7.0 Hz, 1H, —CH=CMe$_2$), 9.75 (s, 1H, —CHO). MS (ESI): 155 (M$^+$+1); bp 206° C. (lit. 207° C.).

Compound 2: (Neo-Isopulegol)

IR (CHCl$_3$): u 2925, 1722, 1643, 1455, 1445, 1375, 1219, 1024, 889, 772 cm$^{-1}$; $^1$H NMR (CDCl$_3$, 300 MHz): δ 0.87 (d, J=6.6 Hz, 3H, —CHMe), 0.92-0.95 (m, 1H), 1.08-1.12 (t, J=6.6 Hz, 1H), 1.47-1.54 (m, 1H), 1.68-1.75 (m, 3H), 1.79 (s, 3H, MeC=CH$_2$), 1.95-1.99 (m, 2H), 3.98 (m, 1H, CHOH), 4.78 (s, 1H, =CH$_2$), 4.95 (s, 1H, =CH$_2$); MS (ESI): 154 (M$^+$).

Compound 3: (Isopulegol)

IR (CHCl$_3$): u 2923, 1645, 1455, 1448, 1375, 1219, 1095, 1051, 1027, 886, 772 cm$^{-1}$; $^1$H NMR (CDCl$_3$, 300 MHz): δ 0.90-1.03 (m, 2H), 0.95 (d, J=6.6 Hz, 3H, —CHMe), 1.30-1.35 (m, 1H), 1.47-1.54 (m, 1H), 1.63-1.65 (m, 1H), 1.69 (d, J=1.5 Hz, 3H, MeC=CH$_2$), 1.87-1.89 (m, 1H), 2.03-2.06 (m, 2H), 3.50 (dt, 1H, J=10.4, 4.2 Hz, CHOH), 4.85 (s, 1H, =CH$_2$); 4.89 (s, 1H, =CH$_2$); MS (ESI): 154 (M$^+$); bp 213° C. (lit. 212° C.).

Compound 4: (Citronellol)

IR (CHCl$_3$): u 3338, 2925, 1452, 1377, 1219, 1058, 1010, 738 cm$^{-1}$; $^1$H NMR (CDCl$_3$, 300 MHz): 6-0.91 (d, J=6.6 Hz, 3H, —CHMe), 1.15-129 (m, 2H, —CHMeCH$_2$CH$_2$—), 1.33-1.45 (m, 2H, —CH$_2$CH$_2$OH), 1.51-1.53 (m, 1H, —CHMe-), 1.60 (s, 3H, =CMe), 1.68 (s, 3H, =CMe), 1.96-2.01 (m, 3H, =CCH$_2$— & OH), 3.61-3.74 (m, —CH$_2$OH), 5.07 (t, J=7.0 Hz, 1H, —CH=CMe$_2$); MS (ESI): 157 (M$^+$+1); bp 223° C. (lit. 222° C.).

Figure 1C:
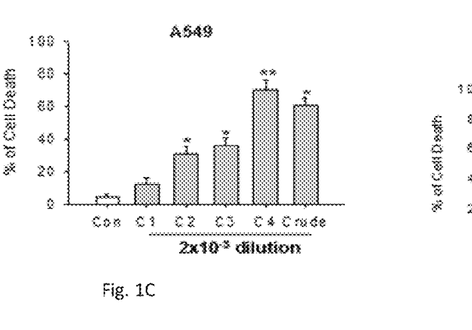
Figure 1D:
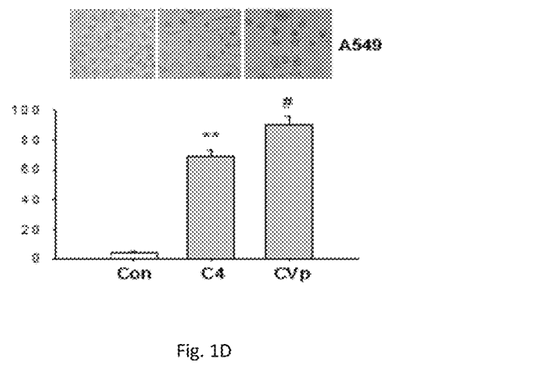
Figure 1E:
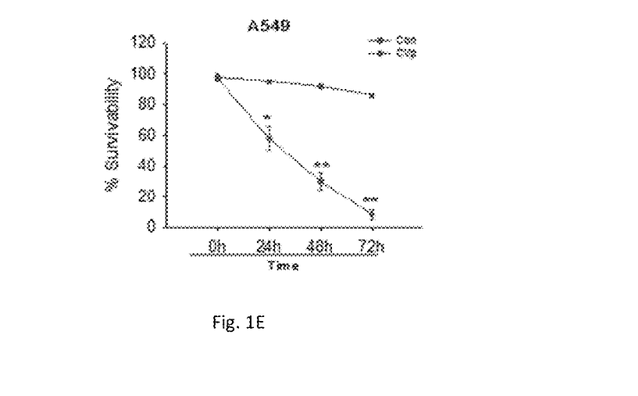

Cell viability was determined by MTT assay. Viability of A549 lung cancer cells was reduced in dose dependent manner when exposed with the varied dilutions of *Litsea cubeba* seed crude extract (FIG. 1A). The crude extract, of *Litsea cubeba* seed was characterized and four major compounds were isolated. The chemical compounds were further characterized and identified as Citronellal (C1) (henceforth referred as compound 1), Neo-isopulegol (C2) (henceforth referred as compound 2), Isopulegol (C3) (henceforth referred as compound 3), and Citronellol (C4) (henceforth referred as compound 44, (FIG. 1B). Cell viability assays were performed to assess the anti-cancer activity in different compounds both individually (FIG. 1C) or compounds C2, C3 and C4 in combination (CVp, FIG. 1D). A-549 lung cancer cells exposed without or with CVp for different time periods and on termination of incubation cell viability was analysed by trypan blue dye exclusion assay (FIG. 1E).

Example 2

Figure 2A:
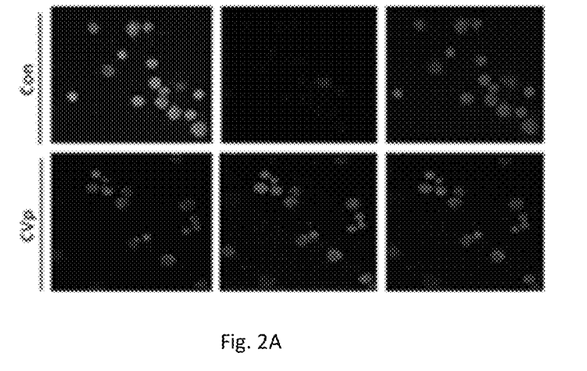
Figure 2B:
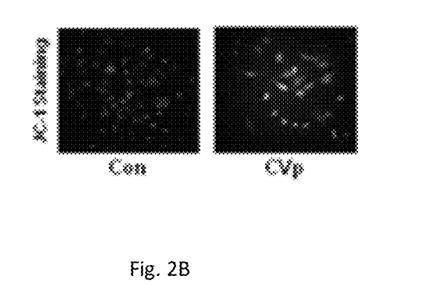
Figure 2C:
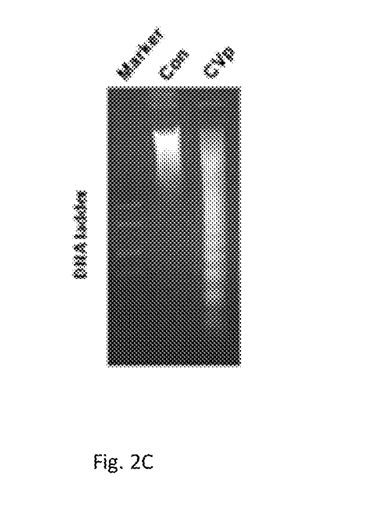

Phosphatidylserine translocation from the inner to the outer leaflet of the plasma membrane is one of the early features of apoptosis. Cell surface phosphatidylserine was detected by phosphatidylserine-binding protein annexin V conjugated with Cy3 using the commercially available AnnexinV-Cy3 Apoptosis detection kit (Sigma-Aldrich). This was used to differentiate between live (green fluorescence), necrotic (red fluorescence) and apoptotic cells (green and red fluorescence). A549 cells treated with CVp for 36 h showed both green and red stains whereas control (untreated) cells stained green only (FIG. 2A). This indicates CVp induces apoptotic cell death. To further confirm the same, JC-1 mitochondrial membrane potential assay with CVp on A-549 lung cancer cells was performed. Loss of mitochondrial membrane potential results in Cytochrome-c release which leads to apoptosis. Mitochondrial membrane potential is an important parameter of mitochondrial function and is a good indicator to determine cell status—normal or apoptotic. JC-1 (5,5,6,6 tetrachloro 1,1',3,3' tetraethyl benzimidazolyle carbocyanine iodide) a lipophilic cationic dye which selectively enter into mitochondria and reversibly changes colour from green to red as membrane potential increases. In healthy cells with high mitochondrial membrane potential, JC-1 spontaneously forms complexes known as J-aggregates with intense red fluorescence. On the other hand in apoptotic cells with low mitochondrial membrane potential, JC-1 remains in monomeric form which shows only green fluorescence. It was observed that CVp exposed A549 cells showed stained with only green fluorescence indicating lower mitochondrial membrane potential, which is a hallmark of induction of apoptosis (FIG. 2B). DNA fragmentation is a hallmark of apoptosis. To detect this, CVp treated A-549 cells was subjected to agarose gel electrophoresis. Exposure of CVp induces DNA fragmentation in A549 cells (FIG. 2C).

Example 3

Figure 3A:
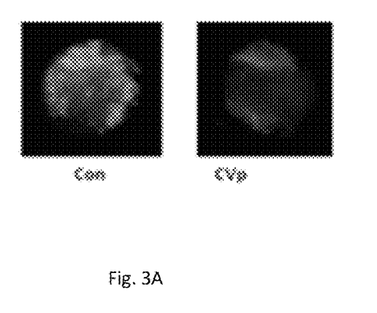
Figure 3B:
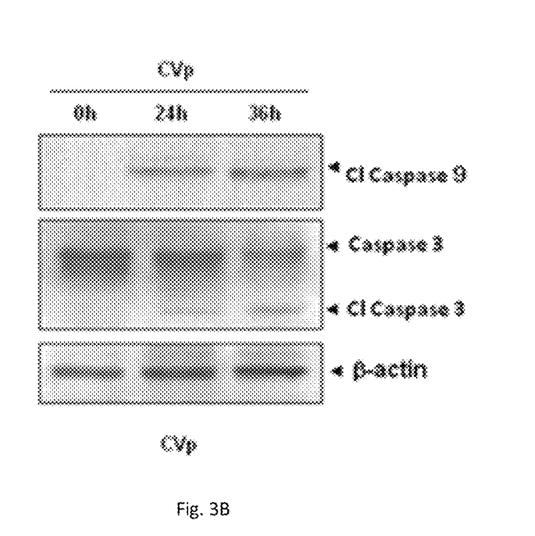
Figure 3C:
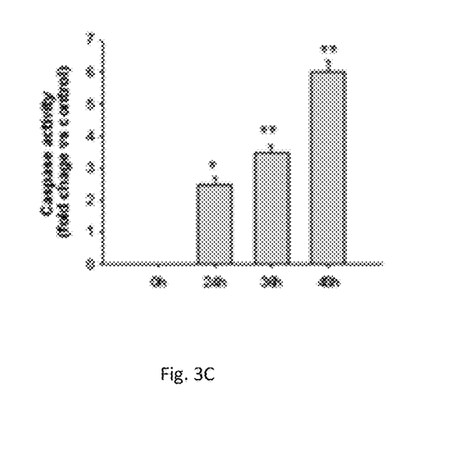
Figure 3D:
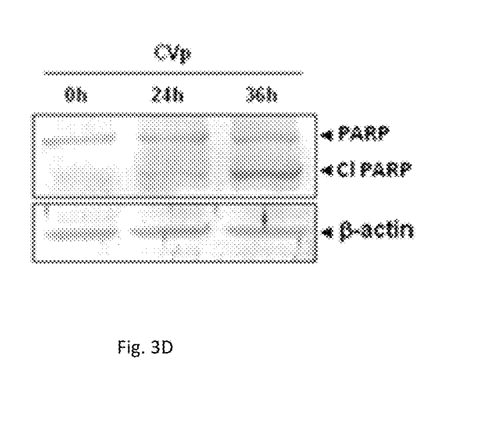

Release of cytochrome C from mitochondria is a key event for the induction of Caspases activation which mainly responsible for apoptotic cell death. We therefore detect the cytochrome C release from mitochondria of A549 cells exposed with CVp. Fluorescence microscopic study revealed that CVp strongly induces leakage of Cytochrome-c from the mitochondria to the cytosol (FIG. 3A). Since caspases are responsible for execution of apoptosis, the caspase activity was also determined. Caspases are the mediators of apoptosis, thus activation of caspase pathway was observed by caspase 9 and caspase 3 cleavages. The combined vapor (CVp) from C2, C3, C4 induces cleavage of caspase 9 and caspase 3 which suggests the induction of apoptotic pathway (FIG. 3B). Caspase 3/7 activity in A-549 cell line has also been observed to demonstrate caspase activity in response to CVp (FIG. 3C). Activation of caspases leads to the activation of caspase mediated DNase which cleaves and destroys a key DNA repair enzyme, PARP. We have observed that CVp exposure to A549 cells induces cleavage of PARP (FIG. 3D), therefore DNA damage induced by caspase mediated DNase could not be repaired due to the unavailability of this enzyme.

Example 4

Figure 4A:
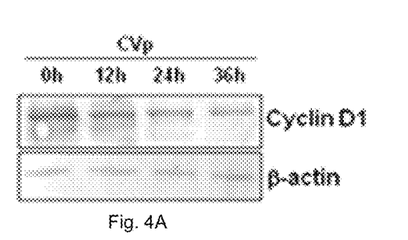
Figure 4B:
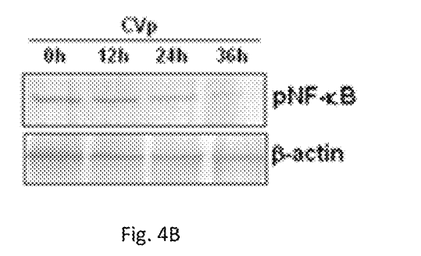
Figure 4C:
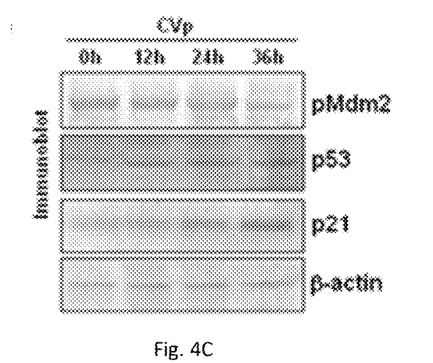
Figure 4D:
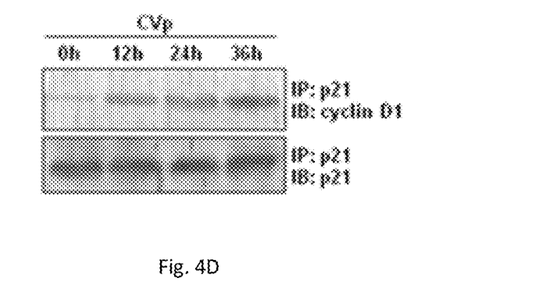
Figure 4E:
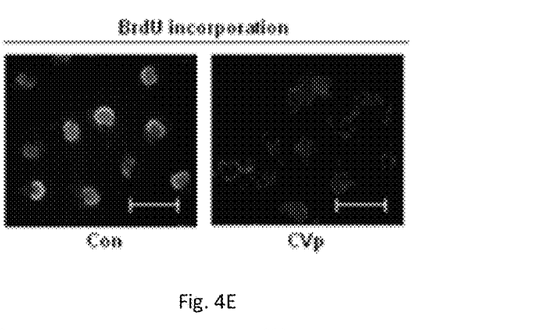

Cyclin D1 is a key regulator of cell cycle progression, it is found to be overexpressed in lung adenocarcinoma which is related to its increased proliferation. FIG. 4A demonstrates that cyclin D1 expression was markedly subdued by CVp exposure. Since NF-κB is its transcription regulator, CVp is expected to effect NF-κB activity. Phosphorylation of NF-κB was significantly inhibited by CVp (FIG. 4B) suggesting this to be the reason for reduced cyclin D1 expression. Augmented cyclin D1 activity for the enhancement of cell cycle progression in cancer cells could not occur in the presence of p53, because it enhances p21 expression and that in turn blocks cyclin D1 binding to CDK4 or CDK6 required for cell cycle progression through G1 phase. CVp exposure of A549 overexpressed p53 which consequently increased p21 protein expression. This seemed to be due to Mdm2 dephosphorylation (FIG. 4C). To observe whether this overexpressed p21 is associated with cyclin D1 for interfering its activity, we performed immunoprecipitation of p21 by using anti-p21 antibody and then probed with anti-cyclin D1 antibody. Results showed an increased association of cyclin D1-p21 from 12 h to 36 h due to CVp exposure (FIG. 4D). Taken these together, one would expect a regression in cell cycle progress. This would be evident from the suppression of BrdU incorporation in A549 cells indicating a halt in DNA replication (FIG. 4E). FACS analysis showed that there was an arrest of G1 to S phase progression in CVp incubated cells (FIG. 4F) which is due to the inhibition of cyclin D1 expression and activity two prong effect by CVp.

Example 5

Figure 5A:
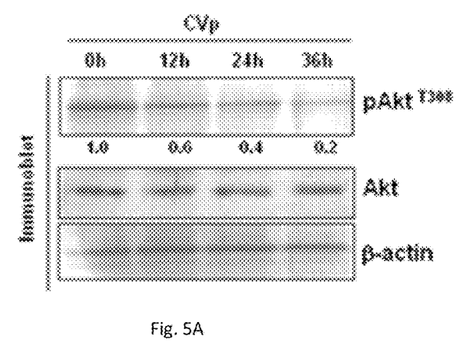
Figure 5B:
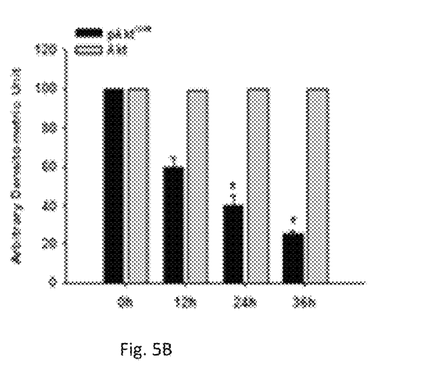
Figure 5C:
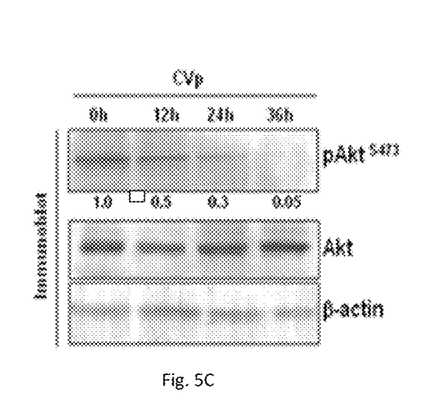
Figure 5D:
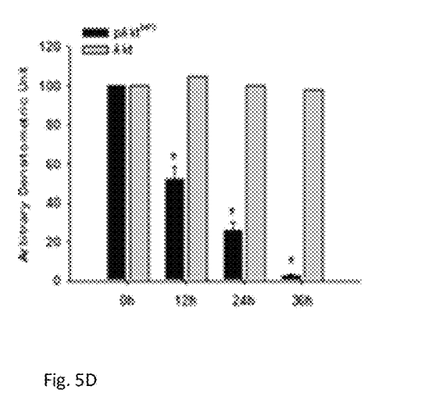

Akt or PKB kinase is a key player in cancer cell survival and proliferation. It is constitutively active in NSCLC (Non-small cell lung cancer), depletion of its active form adversely affected downstream signaling required to promote survival and inhibit apoptosis. This is the reason for any therapeutic intervention of majority of cancer cells, Akt is a primary choice. Therefore, we observed vapour (CVp) effect on Akt phosphorylation. CVp treatment dramatically decreased pAkt ser$^{473}$ and thr$^{308}$ levels in A549 cancer cells (FIG. 5A, B). 36 h, of vapor treatment reduced pAkt at Thr$^{308}$ to 70% and pAkt at Ser$^{473}$ to 95% as compared to 0 h which represented their levels in control cancer cells (FIG. 5B). However Akt protein in A549 cells was not altered due to CVp. This indicates that CVP strongly deactivates Akt which appears to be the major cause for apoptotic death of lung cancer cells.

Example 6

Figure 6A:
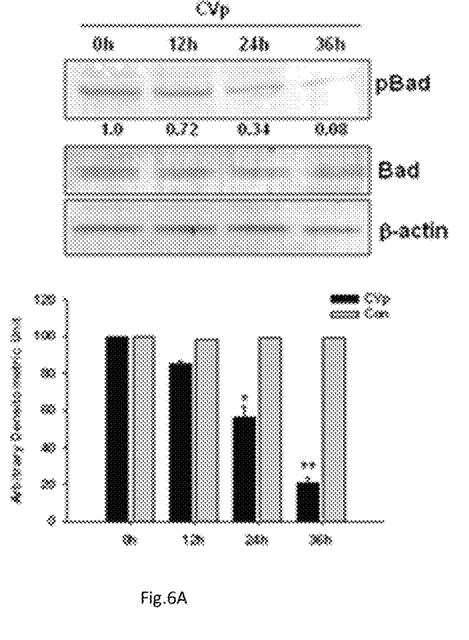

Since Bad is Akt target for initiating apoptosis, we observed CVp effect on Bad. Diminished phosphorylation of Bad [a member of Bcl2 (B-cell lymphoma 2) family] could be identified in A549 cells in response CVp (FIG. 6A), which is an expected consequence due to diminished Akt phosphorylation. Deactivation of Bad results its translocation to the outer mitochondrial membrane that permits it to bind to anti-apoptotic Bcl$_2$ family proteins, Bcl-xL, which release pro-apoptotic protein Bax to promote apoptosis. It could be seen from FIG. 6B that subdued Bcl-xL level due to CVp at 24 h and 36 h with the decline of Bad phosphorylation. This consequently resulted in the elevation of Bax protein which was significantly high at 24 h and 36 h due to CVp exposure in comparison to control cells Once Bcl-xL is displaced and Bad allow Bax to act, following event would be release of cytochrome C from mitochondria. Initiation of apoptotic pathway in A549 cancer cell by CVp was then culminated by the activation of initiator and effector caspases, caspase 9 and caspase 3 respectively, which resulted execution of cell death.

Figure 7:
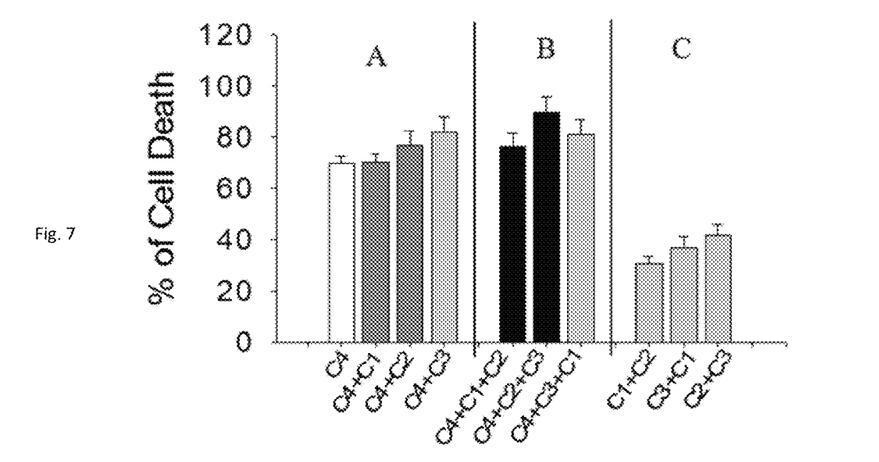
In FIG. 7, column A represents that the combinations of C4+C1 vapor showed similar effect as C4 while C4+C2 had marginal increase but C4+C3 vapor demonstrated significantly high mortality as compared to C4. This was much more prominent with C4+C2+C3 vapor of which exhibited highest effect on mortality of lung cancer cells as shown in column B, whereas C1+C2 or C3+C1 or C2+C3 had no beneficial effect in killing A-549 lung cancer cells as shown in column C. All the compounds were exposed to A549 cells at a concentration of 2×103 dilution. These results suggest that best synergism by the vapor from the volatile chemical compounds could be available with C4+C2+C3 combinations.

Using different combinations, best synergism by the vapor from the volatile chemical compounds could be available with C4+C2+C3 combinations as percentage of cell death of the said composition is 90.0±5.6 for A-549 lung cancer cell line (FIG. 7).

There is a crucial global need to develop a target specific chemo-intervention to retard cancer proliferation or induction of apoptosis or both to tackle the problem of NSCLC and since Akt is best characterized kinase known to support cancer cell survival and progression, its deactivation could have been the best choice for dealing NCSLC.

Therefore, CVp produces two important deleterious effects on lung cancer cells, it induces apoptosis and blocked cancer cell progression, both occurred due to efficient deactivation of Akt. CVp therefore promises to be a valuable therapeutic choice to deal lung cancer. It has another crucial advantage in relation to, bioavailability; CVp could be directly delivered to lung cancer tissue through inhalation.

Present invention demonstrates deactivation of Akt by volatile compounds from the oil extracted and purified from the seeds of *Litsea cubeba*, a plant widely available at North-East region of India. Interestingly, it is the vapor of the oils which induces apoptosis and prevents cell proliferation of NSCLC through the deactivation of Akt. Since it is the vapor, its direct delivery to the lung having NCSLC through inhalation would be possible. Since the vapor of the oils has two prong effects, i.e., induction of apoptotic death and retardation of cell cycle progression, it would be effective in dealing with lung cancer.

Materials and Methods

Cell Culture

The lung cancer cell line, A-549 were cultured in DMEM (Dulbecco's Modified Eagle Medium) containing Earle's salts and non-essential amino acids supplemented with 10% fetal calf serum, penicillin (100 U/ml) and streptomycin (100 μg/ml) in a humidified 95% O2/5% CO2 atmosphere at 37° C. Confluent cells were subcultured by trypsinization and subsequently seeded in 6 well culture plates containing DMEM with essential supplements.

Electrophoresis and Immunoblotting

60 μg of protein from control or CVp treated cell lysates were resolved on 10% or 12.5% SDS-PAGE and transferred to PVDF membranes (Millipore, Bedford, Mass.) with the help of Semi-Dry trans blot Apparatus (TE 77 Semi-Dry Transfer Unit from GE Healthcare, formerly Amersham Biosciences). The PVDF membranes were first incubated overnight with different primary antibodies at 4° C. at 1:1000 dilutions followed by respective alkaline phosphatase conjugated secondary antibodies at same dilutions at 25° C. for three hour duration. The protein bands were detected by using 5-bromro 4-chloro 3-indolyl phosphate/nitroblue tetrazolium (BCIP/NBT). Intensity of the bands was assessed by Image Lab software (Bio-Rad Gel Doc™ XR+, USA).

Co-Immunoprecipitation (Co-IP) Assay

200 µg of control and CVp treated A549 cells were taken and incubated over night with 10 µl of cyclin D1 antibody at 4° C., then protein A agarose was added and incubated for 4 hours at 4° C., then centrifuged at 10000 rpm for 2 minutes at 25° C., the supernatant was discarded, then washed with 500 µl of 1% CHAPS (3-[(3-cholamidopropyl)dimethylammonio]-1-propanesulfonate) and 500 µl PBS (phosphate buffered saline) respectively, then wash twice with PBS, lastly, 4× sample buffer was added with the pellet and load the sample in the gel and immunoblotted with p21.

Trypan Blue Exclusion Assay

After CVp treatment, cells were washed with PBS, trypsinized and re-suspended in complete growth medium. Trypan blue (0.4%) was added to the cell suspension and both live and dead cells were counted using a heamocytometer.

MTT Assay

Cell viability was determined by performing MTT assay (Chemicon, Temecula, Calif., USA) according to manufacturer's instructions. Briefly, cells were plated in 96 well plates. Overnight after cell plating, cells were incubated with CVp. Briefly, 10 µL of 3-(4,5-dimethylthiazol-2-yl)-2-5-diphenyl tetrazolium bromide (MTT) was added to each well for 4 h at 37° C. After solubilization in 100 µL 1(N) isopropanol/0.04(N) HCl, absorbance was read at 595 nm in microplate reader (Thermo Electron Corporation, MA, USA).

JC1 Assay

A549 cells were seeded in 22 mm coverslips. JC-1 staining was performed in control and CVp treated cells, using the JC-1 Mitochondrial Membrane Potential Assay Kit (Cayman Chemical Company, Ann Arbor, Mich., USA) as per the manufacturer's protocol. Briefly, cells were subjected with JC-1 stain (10 µg/ml) for 20 min at 37° C. The shift of fluorescence due to CVp treatment was observed under Zeiss Axio Scope A1 microscope (Carl Zeiss, Germany).

AnnexinV-Cy3 Detection Assay

To investigate the possibility of apoptosis inducing effect of CVp, we used AnnexinV-Cy3 Apoptosis detection kit (Sigma-Aldrich). This test helps us to differentiate between live (green fluorescence), necrotic (red-fluorescence) and apoptotic cells (green and red fluorescence). A549 cells incubated with Cvp were washed with PBS, cells were removed and further dissolved in PBS. 50 µl of cell suspension was spotted on poly lysine coated glass slide and left at room temperature to be adsorbed. After that, cells were washed thrice with binding buffer and stained with double labelling staining solution (Annexin V-Cy3 and 6 Carboxy Fluorescein Di-Acetate (CFDA) for 10 min. Excess labelling agent was removed by washing the cells three times with binding buffer. Results were observed under fluorescence microscope (Zeiss Axio Scope A1 microscope, Carl Zeiss, Germany).

Immunofluorescence Study of Cytochrome C

A549 cells were cultured on sterile uncoated glass cover slips. Both control and CVp treated cells were stained with Mitotracker at 1:12,000 dilutions (in DMEM) for 15 min. Cells were further washed with DMEM and processed for fixation. After fixation, cells were incubated with anti-cytochrome C antibody (1:100) for 2 h followed by incubation with FITC-conjugated secondary antibody (1:50) for another 1 h at room temperature. Cells were counter stained with DAPI for nuclear staining and mounted with DABCO (1,4-diazabicyclo[2.2.2]octane) and observed under Zeiss Axio Scope A1 fluorescence microscope (Carl Zeiss, Gottingen, Germany).

DNA Fragmentation Assay

DNA was extracted from $1 \times 10^6$ control (DMSO only) or CVp treated A-549 cells by using DNA apoptosis laddering kit from Roche Diagnostics, (GmbH, Germany) following the manufacturer's instruction. Eluted DNA samples were then loaded on 1.2% agarose gel stained with ethidium bromide and image was captured by Bio-Rad gel documentation system using Image Lab software.

Caspase-Glo 3/7 Assay

A549 cells were seeded in 96 well culture plates and incubated with CVp for different time periods. On termination of incubations caspase activity was measured by using the Caspase-Glo™ 3/7 assay kit (Promega, Wis.) according to the manufacturer's protocol. Briefly, Caspase-Glo 3/7 solution was added to the culture media and incubated at 37° C. for 30 min. Luminescence was measured in a DTX-800 multimode detector (Beckman Coulter, Calif., USA).

BrdU Incorporation Assay

DNA synthesis was monitored by measuring incorporation of thymidine analogue 5-bromo-2'deoxyuridine (BrdU) in growing cancer cells using BrdU labeling and detection kit (Roche Diagnostics, GmbH, Germany). Control A549 and CVp treated A549 cells were grown and plated in coverslips. After the incubation period, cells were refreshed with complete medium containing BrdU labeling reagent and incubated for 3 h. Cells were then washed thoroughly with wash buffer and fixed with ethanol fixative for 20 min at −20° C. Fixed cells were washed and incubated with anti-BrdU antibody solution followed by anti-mouse Ig fluorescein solution. Cells were then mounted on glass slides and observed under fluorescence microscope (Zeiss Axio Scope A1 microscope, Carl Zeiss, Germany).

Flow-Cytometric Analysis

A549 cells were cultured in 6-well plates ($1.5 \times 10^6$ cells per well) and treated with CVp or complete DMEM medium (for the control group) and incubated for 24 and 48 hours. Culture supernatant from each group was pooled and cells were fixed for 12 h with 1 ml of 75% ethanol ($1 \times 10^6$ cells/ml) and transferred to 2 ml microfuge tubes for flow-cyto-metry and propidium iodide (PI) staining. For PI staining, the cells were washed twice with cold PBS and centrifuged at 1000 g for 5 min. The pellet was washed twice in cold 0.1% Triton X-100 PBS and incubated at room temperature for 30 minutes with 300 µl DNA dye (containing 100 g/ml propidium iodide and 20 U/ml RNase; Sigma-Aldrich). Flow cytometry (BD-Bioscience) analysis was performed. The cells were collected for the calculation of DNA amount for cell cycling analysis using MULTY-CYCLE software (PHEONIX, Co. USA). The extent of apoptosis was analyzed and quantified using WinMDI version 2.9 (Scripps Research Institute, La Jolla, Calif., USA).

Results

Bioactivity Guided Isolation and Purification of Oils from the Seed of *Litsea cubeba*

Chromatographic purification of *Litsea cubeba* seed essential oils gave rise four types of compounds, i.e., C1 (compound 1), C2 (compound 2), C3 (compound 3) and C4 (compound 4) and they were separately added at a dilution of 1:1000 in one of 6 well of culture plate, other 5 wells contained A549 cell which is adenocarcinoma of NSCLC cells, each, had 1×10$^6$ cells. Hence, each 6 well plate had one type of compound. The vapors generated from each of these wells were exposed to cells at 1:2000 dilution for 48 h. It could be seen from FIG. 1C that C1 had-poor activity, C2 and C3 had more than 56% higher activity as compared to C1, while C4 had-highest activity so far lung cancer cell death is concerned. Each compound was then identified through 1H N spectrum with authentic compound and their chemical nature was detected as follows—C1: citronellal; C2: neo-isopulegol; C3: isopulegol and C4: citronellol (FIG. 1B). We observed that C2, C3 and C4 at 1:1:1 ratio to observe whether these combinations had additional or synergistic effect on cell death in comparison to C4 vapor over this combination exhibited significantly greater activity in killing A549 cells in comparison to the vapor of C4 alone (FIG. 1D). We therefore used the vapor from these combined compounds which is henceforth termed as Combined Vapour (CVp=C2+C3+C4). When CVp was exposed at different time periods, death of cells occurred in a linear fashion (FIG. 2E), indicating a biological relevance i.e., this death may not be due to necrosis.

We therefore examined whether CVp induced death of cells was due to apoptosis and used double fluorescence staining with annexin V-Cy3 and 6-CFDA for differentiating the live, apoptotic, and necrotic cells. CVp-induced phosphatidylserine translocation from the inner to the outer leaflet of the plasma membrane was detected by the phosphatidylserine-binding protein annexin V conjugated with Cy3. Control A549 cells showed staining only with 6-CFDA (green) whereas treatment with CVp increased the number of double-stained cells with annexin V-Cy3 and 6-CFDA (red and green), suggesting that these cells were undergoing apoptotic cell death (FIG. 2A). To extend our observation further, we used JC-1 fluorescent dye. In live cells, JC-1 remains associated with the mitochondria that emit red fluorescence while depolarized mitochondrial membrane in apoptotic cells would permit its cytosolic content to interact with JC-1 that emits green fluorescence. It could be seen from FIG. 2B that live A549 cells were emitting red fluorescence whereas CVp incubated cells were marked with green fluorescence indicating cellular apoptosis. CVp induced apoptotic cell death in lung cancer cells was also evident DNA ladder due to oligonucleosomal fragmentation of chromatin (FIG. 2C). These results indicate that CVp induced death of lung cancer cells occurs through apoptotic pathway.

CVp Induces Apoptosis in Lung Cancer Cells

It was mentioned above that CVp exposure caused lung cancer cell mortality, which was likely through the induction of caspase pathway. To assess this, further we determined whether CVp stimulates release of cytochrome f from mitochondria by labeling cytochrome C with FITC and detecting mitochondria with mitotracker. FIG. 3A shows that due to CVp, considerable amount of cytochrome C was released into cytosol, indicating initiation of apoptosis. Activation of caspases is the major event in apoptotic cell death. On receiving the death signal, inactive caspases, which are present in zymogens, initiator caspase 9 gets activated and cleaved, this cleaved product in turn activates effector caspase 3. CVp treatment in A549 cells effected increased cleaved caspase 9 formation which caused conversion of caspase 3 into cleaved caspase 3 indicating its activation by CVp (FIG. 3B), we further analysed caspase 3 enzyme activity which increased to 6 fold over the control cancer cells at 48 h (FIG. 3C). Time dependent increase of caspase 3 activity due to CVp was also reflected from poly [ADP-ribosyl]-polymerase or PARP cleavage. PARP is a DNA repair enzyme, it is one of the substrates of caspase 3 and it would be evident from FIG. 3D that PARP cleavage in A549 cells was substantially increased at 36 h at the time when caspase 3 activity was in peak. This indicates irreparable damage of DNA due to CVp, an event that occurs during apoptosis.

Impairment of Cyclin D1 by CVp

Figure 4F:
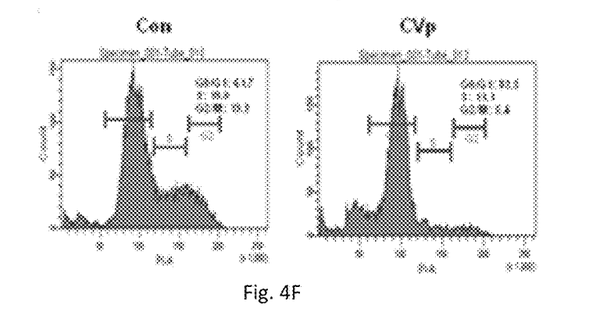

Cyclin D1 is a key regulator of cell cycle progression, it is found to be overexpressed in lung adenocarcinoma which is related to its increased proliferation. FIG. 4A demonstrates that cyclin D1 expression was markedly subdued by CVp exposure. Since NF-κB is its transcription regulator, CVp is expected to effect NF-kB activity. Phosphorylation of NF-kB was significantly inhibited by CVp (FIG. 4B) suggesting this to be the reason for reduced cyclin D1 expression. Augmented cyclin D1 activity for the enhancement of cell cycle progression in cancer cells could not occur in the presence of p53, because it enhances p21 expression and that in turn blocks cyclin D1 binding to CDK4 or CDK6 required for cell cycle progression through G1 phase. CVp exposure of A549 overexpressed p53 which consequently increased p21 protein expression. This seemed to be due to Mdm2 dephosphorylation which is expected as Mdm2 is a substrate of Akt (FIG. 4C). To observe whether this overexpressed p21 is associated with cyclin D1 for interfering its activity, we performed immunoprecipitation of p21 by using anti-p21 antibody and then probed with anti-cyclin D1 antibody. Results showed an increased association of cyclin D1-p21 from 12 h to 36 h due to CVp exposure (FIG. 4D). Taken these together, one would expect a regression in cell cycle progress. This would be evident from the suppression of BrdU incorporation in A549 cells indicating a halt in DNA replication (FIG. 4E). FACS analysis depicts the result of cyclin D1 expression and activity inhibition, a two prong effect by CVp. FIG. 4F shows that there was an arrest of G1 to S phase progression in CVp incubated cells, where G0/G1 phase cells.

Inhibition of Akt Phosphorylation by CVp Adversely Affects Downstream Signaling for Cell Survival.

Figure 6B:
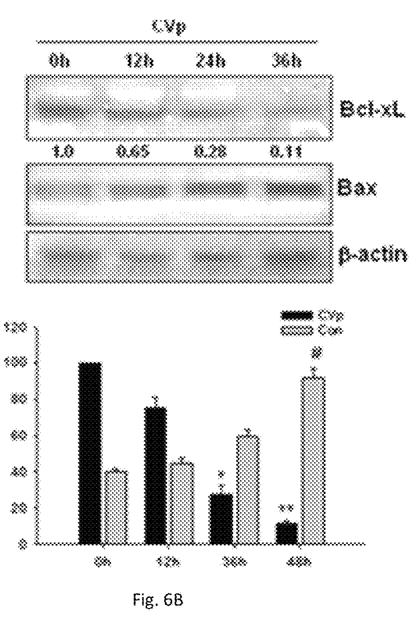

Vapour (CVp) effect in killing of lung carcinoma cells where it was indicated to be due to apoptosis, we planned to observe deactivation of Akt depending on our previous studies with prostate cancer. Moreover, for any therapeutic intervention of majority of cancer cells, Akt is a primary choice. Ser$^{473}$ and Thr$^{308}$ phosphorylation of Akt activates this kinase to phosphorylate its target protein to promote survival and inhibit apoptosis. Vapor treatment dramatically decreased pAkt Thr$^{308}$ and Ser$^{473}$ levels in A549 cancer cells (FIG. 5AB). 36 h of vapor treatment reduced pAkt Thr$^{308}$ to 70% and pAkt Ser$^{473}$ to 95% as compared to 0 h which represented their levels in control cancer cells. However Akt protein in A549 cells was not altered due to CVp. This indicates that CVP strongly deactivates Akt which appears to be the major cause for apoptotic death of lung cancer cells. Since Bad is Akt target for initiating apoptosis, we observed CVp effect on Bad. Phosphorylation of Bad was decreased to 80% in response CVp (FIG. 6A), which is an expected consequence due to diminished Akt phosphorylation. However, Bad protein in cancer cells remains unaltered. Deactivation of Bad results its translocation to the outer mitochondrial membrane that permits it to bind to anti-apoptotic protein Bcl$_2$ family proteins, Bcl-xL, which release pro-apoptotic protein Bax to promote apoptosis. It could be seen from FIG. 6B that subdued Bcl-xL level due to CVp at 24 h and 36 h with the decline of Bad phosphorylation. This consequently resulted in the elevation of Bax protein which was significantly high at 24 h and 36 h due to CVp exposure in comparison to control cells (FIG. 6B). Once Bcl-xL is displaced and Bad allow Bax to act, following event would be release of cytochrome C from mitochondria. We assessed cytochrome C level in the cytosol and observed that it was increased to more than % over the control cancer cells, indicating progression of apoptotic pathway. FIG. 7 showed that Combined Vapour (CVp) of C2+C3+C4 at 1:1:1 ratio is most effective than any other combinations.

TABLE 1 representing activity of Compound C1, C2, C3, C4 and C2 + C3 + C4 in vapour form

| Extract/Compounds | Activity in vapour form % of cell death for Lung Cancer cell Line (A-549) |
|---|---|
| Plant Seed Extract | 60.0 ± 2.5 |
| Compound C1 | 12.5 ± 3.6 |
| Compound C2 | 30.5 ± 5.0 |
| Compound C3 | 36.0 ± 4.5 |
| Compound C4 | 70.0 ± 6.0 |
| Compound C2 + Compound C3 + Compound C4 | 90.0 ± 5.6 |

ADVANTAGES OF THE INVENTION

The main advantages of the invention are:
The source is herbal.
The composition has no side effects or toxicity.
The compounds are highly effective for treating different types of cancer.
Vapor form utilizes less concentration of crude extract; approximately in atto mole concentration.
Since this is effective in lung cancer, the delivery would be very easy that is through inhalation. Moreover, as inhaler, its availability as medicine in future would be easier.
These compounds had no hazardous effect on normal cell like hepatocytes, adipocytes and would select only malignant cells.

What is claimed is:

1. A synergistic pharmaceutical composition having compound C1 (citronellal) removed to induce cell death in cancer cell lines, wherein the said composition comprising Compounds C2 (Neo-isopulegol), C3 (Iso-pulegol) and C4 (Citronellol) in the form of a vapor absent C1 and wherein each of the Compounds C2, C3, and C4 are extracted, purified, and combined at a volume ratio of 1:1:1.

2. A composition as claimed in claim 1, wherein the compounds used are derived from ripe seeds of the plant *Litsea cubeba*.

3. A composition as claimed in claim 1, wherein the said compounds used are administered individually or in synergistic pharmaceutical composition in the vapor form to induce cell death in the cancer cell lines by apoptosis.

4. The composition as claimed in claim 1, wherein percentage of cell death of the said composition is 90.0.+−0.5.6 for lung cancer cell line.

* * * * *